United States Patent
Choi et al.

(10) Patent No.: US 6,791,003 B1
(45) Date of Patent: Sep. 14, 2004

(54) DUAL ADHESIVE TRANSDERMAL DRUG DELIVERY SYSTEM

(75) Inventors: Young Kweon Choi, Daejeon (KR); Hyun Suk Yu, Daejeon (KR); Hye Jeong Yoon, Daejeon (KR); Ho Chin Kim, Daejeon (KR)

(73) Assignee: Samyang Corporation, Seoul (KR)

( * ) Notice: Subject to any disclaimer, the term of this patent is extended or adjusted under 35 U.S.C. 154(b) by 53 days.

(21) Appl. No.: 10/110,843

(22) PCT Filed: Oct. 6, 2000

(86) PCT No.: PCT/KR00/01115

§ 371 (c)(1),
(2), (4) Date: Aug. 9, 2002

(87) PCT Pub. No.: WO01/26705

PCT Pub. Date: Apr. 19, 2001

(30) Foreign Application Priority Data

Oct. 11, 1999 (KR) ........................ 1999-43794

(51) Int. Cl.[7] .................................. A61F 13/00
(52) U.S. Cl. .................. 602/48; 604/305; 424/449
(58) Field of Search ............... 424/443–449; 602/48; 604/305–308

(56) References Cited

U.S. PATENT DOCUMENTS

| | | | |
|---|---|---|---|
| 4,588,580 A | | 5/1986 | Gale et al. ................... 424/21 |
| 4,666,441 A | | 5/1987 | Andriola et al. ........... 604/897 |
| 5,186,939 A | * | 2/1993 | Cleary et al. ............... 424/448 |
| 5,352,456 A | | 10/1994 | Fallon et al. ............... 424/448 |
| 5,494,680 A | * | 2/1996 | Peterson ..................... 424/448 |
| 5,505,956 A | * | 4/1996 | Kim et al. .................. 424/448 |
| 5,643,187 A | * | 7/1997 | N.ae butted.stoft et al. .. 602/43 |
| 5,948,433 A | * | 9/1999 | Burton et al. ............... 424/448 |
| 6,129,929 A | * | 10/2000 | Wick .......................... 424/448 |

* cited by examiner

Primary Examiner—John J. Calvert
Assistant Examiner—Linh Truong
(74) Attorney, Agent, or Firm—Jones Day

(57) ABSTRACT

A dual drug containing adhesive transdermal drug delivery system comprising: a support layer, a first drug containing adhesive layer and a second drug containing adhesive layer each of said layers having a proximal and distal surface wherein each layer is positioned adjacent to the other with each layer having its distal surface laminated to said support layer, and a peelable backing layer positioned over and laminated to the proximal surface of said first and second adhesive layers is disclosed.

13 Claims, 2 Drawing Sheets

(a)

(b)

(c)

(d)

DUAL ADHESIVE TRANSDERMAL DRUG DELIVERY SYSTEM

BACKGROUND OF THE INVENTION

1. Field of Invention

This invention relates generally to transdermal and transmucosal drug delivery (DD) devices. More particularly, the present invention relates to dual drug loaded adhesive laminated TDD devices for delivering drugs at different rates, e.g., the delivery of fentanyl and its analgetically effective derivatives for the relief of postoperative and terminal cancer pains.

2. Description of the Prior Art

The efficacy of some systemically acting drugs may be optimized by administering them in a manner that rapidly produces therapeutically effective blood levels. The most common method to achieve such a goal is by bolus injection. Oral administration, depending upon the ability of the drug to be absorbed into the circulation via the gastrointestinal tract, may also afford a rapid onset of therapeutically effective blood levels. Transdermal drug delivery while often viewed is an advantageous mode of administration over injection or oral dosing, especially for establishing constant long term drug delivery, is not normally considered to be a practical means for rapidly achieving high blood levels of drugs. This is because most transdermal drug delivery devices operate in a manner that results in a significant lag time (the time needed for a given therapeutic agent to reach an effective blood concentration following administration) between placing the device on the skin and realizing the required or desired blood levels.

Representatives of drugs where a rapid onset of activity is desired are analagesics used to control or treat postoperative and terminal cancer pains. Fentanyl and its analgetically effective derivatives (hereafter referred to as "derivatives" such as sufentanyl, carfentanyl, lofentanyl and alfentanyl and analogous bases and salts thereof, have long been known as extremely potent and effective anesthetics and analgesics. The chemical nomenclature for fentanyl is N-phenyl-N-[1-2-phenylethyl)-4-piperidinyl]propanamide. Fentanyl has been used as a synthetic opioid to alleviate postoperative or terminal cancer pains due to the fact that its analgesic effects are 50–100 times more potent than morphine. The effective analgesic plasma concentration of fentanyl varies from subject to subject, however, the mean concentration of fentanyl is about 1 ng/mL and 3 ng/mL for postoperative administration and intraoperative administration, respectively. Plasma concentrations of fentanyl up to 10 ng/mL have been shown to be effective in treating pain experienced in the terminal stages of a cancer and similar situations.

Fentanyl has been traditionally administered via intravenous or intramuscular injection as a way to relieve pain. It is normally administered either as a bolus injection, infusion or continuous infusion. These conventional methods, although providing an analgesic effect, have been known to have some drawbacks. For example, fentanyl has to be administered in multiple doses and in an excessive amount because fentanyl has a relatively short biological activity half-life (3.7 hrs in plasma concentration and 0.78L/hr/kg in systemic clearance). Further, repeated administration of excessive amounts of fentanyl can lead to development of tolerance and physical dependence to fentanyl, as is often the case with other opioid drugs. In addition, intravenous injection of fentanyl may result in hypopnea.

The application of transdermal drug delivery technology to the administration of a wide variety of drugs has been proposed and various systems for accomplishing this have been disclosed. Recently, transdermal delivery systems for fentanyl were developed to remedy the above-mentioned drawbacks of traditional methods. Transdermal delivery systems can minimize the usual rejection of fentanyl administration by a patient due to side effects such as tolerance and physical dependence, which result from the pulsed nature of an oral or an injectable agent during delivery into the body and can maintain fentanyl concentrations at a constant level during administration thus eliminating the peak-and-valley phenomenon of blood levels often seen during drug injection. Furthermore, the fact that the drastic increase in blood concentration of fentanyl immediately after an injection may be too toxic, supports the idea that transdermal delivery systems will be more advantageous both in terms of safety and efficacy.

U.S. Pat. No. 4,626,539 discloses the transdermal delivery of an opioid and the use of various vehicles to enhance the penetration through skin of an opioid. U.S. Pat. No. 4.583,580 discloses a reservoir type transdermal delivery system of fentanyl that is already commercialized. The device disclosed uses ethanol as A permeation enhancer and the mixture of fentanylthanol is contained in the reservoir in a fluid form. However, a significant amount of fentanyl still remains unused even after completion of administration and this raises a safety problem in that leftover fentanyl can be recovered and misused for purposes other than the intended therapeutic use. Moreover, this system requires a multi-step manufacturing process and also requires a lag time of up to ten hours following administration for optimal analgesic effect to be realized thus necessitating the initial administration to be conducted in combination with an injection for more effective treatment of pain.

A common problem encountered with use of transdermal delivery systems is the presence of lag time. U.S. Pat. No. 5,352,456 discloses a transdermal drug delivery system that enables higher amounts of the therapeutic agent to be delivered systemically upon application by establishing a volatile penetration-enhancing layer within a laminated layer.

U.S. Pat. No. 5,820,875 discloses a reservoir drug delivery system combining a non- volatile permeation enhancer and a volatile penetration enhancer which provides an initial burst of a given therapeutic agent to the dermis. However, the extent of volatilization of a given therapeutic agent differs depending on the environment of the system being used, and it is difficult to maintain the skin flux of a given therapeutic agent at a constant level thus making the manufacturing process more complicated and consistent drug delivery somewhat variable.

U.S. Pat. No. 5,186,939 discloses a laminated transdermal system for administration of fentanyl which is characterized by using propylene glycol monolaurate as a penetration enhancer and a silicone adhesive as a reservoir for the therapeutic agent. However, this system cannot contain more than 2 wt % of a therapeutic agent due to the relatively low solubility of fentanyl in the silicone adhesive. There is a shorter duration of delivery of the therapeutic agent as compared to that in the abovementioned U.S. Pat. No. 4,588,580 because the reservoired therapeutic agent is rapidly released, e.g., within 24 hrs. This system is therefore unable to maintain a constant and sustained blood concentration of the therapeutic agent.

U.S. Pat. No. 5,843,472 discloses a drug delivery system for the transdermal administration of tramsulosin. The system is a laminated composite comprising a backing layer, a drug reservoir, and adhesive means for affixing the composite to the skin. The reservoir is comprised of a polymeric matrix material containing tamsulosin and a permeation enhancer. In a preferred embodiment, the system contains two drug reservoirs comprised of polymeric adhesive material, one overlays to another and they are separated by an absorbent source layer of a nonwoven fabric.

U.S. Pat. No. 5,626,866 discloses a method for making a transdermal drug deliver) device for heat sensitive and volatile drugs. The device for administering a drug to the skin consists of a drug-containing adhesive composite layer having an impermeable backing material laminated to the distal surface thereof and a proximal peelable impermeable backing material so adapted. The drug, in gelled form is extruded onto at least one exposed surface of the first or second adhesive laminate followed by laminating together the exposed surfaces of the first and second adhesive laminate such that the adhesive layers and gelled drug are combined to form the drug containing adhesive composite.

Some drugs, such as fentanyl and its derivatives, are highly potent, rapidly metabolized drugs having a relatively narrow therapeutic index, which produce extremely undesirable side effects when overdosed, most notably respiratory depression which if left unchecked could cause death. These drugs are also relatively expensive and have a high potential for abuse. Therefore, it would be desirable that the device deliver the drug at a substantially constant rate for a sustained period of time, e.g. aleast 24 hours, while at the same time not having a long lag time. This device would also keep the amount of drug within the depleted system to a minimum. It is also desirable that the device have a controlled delivery rate so that excessive amounts of drugs are not delivered.

SUMMARY OF THE INVENTION

Accordingly, the present invention provides a drug-containing laminated transdermal delivery system wherein the drug can be rapidly released during the early stages of administration and rapidly reach a therapeutic level systemically, and then maintain a persistent long-term therapeutic effect.

One embodiment of the present invention is a fentanyl-containing laminated transdermal delivery system which is useful for treating the acute pains that accompany any surgery or chronically experienced during terminal illness such as cancer.

The drug-containing laminated transdermal delivery system of the present invention comprises at least two adjacent drug containing pressure-sensitive adhesive(PSA) layers having different solubilities for the drug. One surface of each layer is laminated to an impermeable backing support and the opposing surface is adapted to be applied to and adhere to the skin of a wearer. For manufacturing and storage purposes, the surface to be attached to the skin is covered with a peelable backing layer which is stripped off prior to use. Each adhesive layer has a certain surface area or ratio of one layer to the other contingent upon factors affecting the delivery of drug therefrom such as the solubility of the drug in each adhesive. Therefore, in the device of the present invention, a certain amount of the drug can be rapidly released in the early stage of administration from the adhesive polymer layer which has a relatively low solubility of the drug, thus triggering earlier onset of the therapeutic effect of the by reducing the time needed to reach a therapeutic blood level. After a certain duration of time of administration, the drug can be released at a constant rate from the adhesive polymer layer which has a relatively high solubility of the drug and so maintains a persistent long-term analgesic effect The present invention is particularly useful for the trans-dermal delivery of highly potent rapidly metabolized drugs having relatively narrow therapeutic indexes which may produce extremely undesirable side effects when overdosed, such as fentanyl and its derivatives, which are excellent therapeutic agents for treating acute postoperative or terminal cancer pains.

The present invention also provides methods of making and using a transdermal drug delivered device wherein the drug can be rapidly released during the early stages of administration to reach a therapeutic level systemically and maintain a persistent long-term analgesic effect.

DETAILED DESCRIPTION OF THE INVENTION

Figure 1:
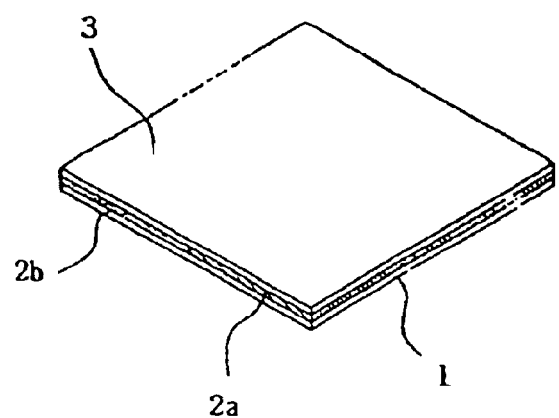
FIG. 1 shows a perspective view of the drug-containing laminated transdermal delivery system according to the present invention, showing a support layer (1), dual laminated drug containing adhesive layers (2a and 2b) and a peelable backing layer (3).

Before the present method of making a pressure-sensitive adhesive matrix patch for transdermal drug delivery is disclosed and described, it is to be understood that this invention is not limited to the particular configurations, process steps, find materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition for delivering "a drug," includes reference to two or more of such drugs, reference to "an adhesive" includes reference to one or more of such adhesives, and reference to "a permeation enhancer" includes reference to two or more of such permeation enhancers.

In describing and claiming the present invention, the following terminology will be used in accordance with the definitions set out below.

As used herein, "effective amount" means an amount of a drug or pharmacologically active agent that is nontoxic but sufficient to provide the desired local or systemic effect and performance at a reasonable benefit/risk ratio attending any medical treatment. An effective amount of a permeation enhancer as used herein means an amount selected so as to provide the selected increase in skin permeability and rate of administration.

As used herein, "drug," "pharmaceutical agent," "pharmacologically active agent," or any other similar term means any chemical or biological material or compound suitable for transdermal administration by the methods previously known in the art and/or by the methods taught in the present invention that induces a desired biological or pharmacological effect The effect can be local, such as providing for a local anesthetic effect, or it can be systemic This invention is not drawn to novel drugs or new classes of active agents. Rather it relates to a dosage form device and the mode of making dosage forms of agents or drugs that exist ill the state of the art or that may later be established as active agents and that fire suitable for delivery by the present invention so as to achieve a dual delivery effect of initial rapid deliver followed by a slower sustained delivery. Such substances include broad classes of compounds normally delivered into the body through body surfaces and membranes, including skin. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral, and cerebral; central nervous system stimulants; vasoconstrictors cough and cold preparations, including decongestants; hormones such as estradiol and other steroids, including corticosteroids; hypnotics; immunosuppressives; muscle relaxants; parasympatholytics; psychostimulants; sedatives; and tranquilizers.

As used herein, "solvent-base pressure-sensitive adhesives" are hydrophobic pressure-sensitive adhesives that are dissolved in organic solvents, and "water-based pressure-sensitive adhesives" are hydrophobic pressure-sensitive adhesives that are water-insoluble and that have been dispersed in water as water-insoluble particles. A pressure-sensitive adhesive is "an adhesive which adheres to a surface at room temperature by temporary application of pressure alone." Shields, Adhesives Handbook 343 (3d ed., 1984). Typical polymers that have been used to form the basis of pressure-sensitive adhesives are natural rubbers, block copolymers, synthetic rubbers (butyl rubber and polyisobutylene), styrene-butadiene rubber (SBR), polyacrylates, D. Satas, Pressure-sensitive Adhesives and Adhesive Products in the United States, in Handbook of Pressure-sensitive Adhesive Technology 4 (D. Satas ed., 2d ed., 1989), ethylene-vinyl acetate copolymers, D. Satas, Miscellaneous Polymers, in Handbook of Pressure-sensitive Adhesive Technology 524 (D. Satas ed., 2d ed., 1989), and silicones, L. A. Sobieski & T. J. Tangney, Silicone Pressure-sensitive Adhesives, in Handbook of Pressure-sensitive Adhesive Technology 508 (D. Satas ed., 2d ed., 1989). The physical state of the adhesive raw materials has been discussed by Benedek and Heymans:

In order to be coated onto the face stock material the adhesive must be in the liquid state. This state may be achieved by melting (hot-melt PSAs), dissolving (solvent-based adhesives), or dispersing (adhesive dispersions) the PSAs. . . . Generally, there are aqueous and solvent-based adhesive solutions, and aqueous or solvent-based adhesive dispersions. The most important are the organic solvent solutions of adhesives (solvent-based adhesives) and the water-based dispersions of adhesives (water-based adhesives).

I. Benedek & L. J. Heymans, Pressure-Sensitive Adhesives Technology 34 (1997).

As used herein, "permeation enhancer,""penetration enhancer,""chemical enhancer," or similar terms refer to compounds and mixtures of compounds that enhance the permeation of a drug across the skin.

Chemical enhancers comprise two primary categories of components, i.e., cell-envelope disordering compounds and solvents or binary systems containing both cell-envelope disordering compounds and solvents. The latter are well known in the art, e.g. U.S. Pat. Nos. 4,863,970 and 4,537,776, incorporated herein by reference.

The present invention provides a dual pressure-sensitive adhesive drug-containing transdermal delivery system comprising adjacent first and second pressure-sensitive adhesives layers of different composition and solubility for the drug to be administered wherein the adjacent pressure-sensitive adhesive layers are attached or laminated on one surface to an impermeable pressure-sensitive backing layer and are covered on the opposite surface with a peelable layer which is stripped off prior to the application of such surfaces to the skin of a user. Each drug containing pressure-sensitive adhesive layer has a certain surface area or surface ratio of one layer to the other so as to optimize the delivery of drug from each layer for its intended purpose. The term "the first layer" or "the first laminated layer" means one layer of the drug containing pressure-sensitive adhesive laminated to the backing or support layer and the term "the second layer" or "the second laminated layer" means the second or adjacent layer of the drug containing pressure-sensitive adhesive laminated to the backing or support layer. The first and the second laminated layer are in adjacent and can be in adjoining positions to each other and they both are laminated on one surface to the impermeable or support layer. Therefore, a certain amount of the drug or therapeutic agent can be rapidly released from the fist layer which is an adhesive polymer which has a relatively low solubility of the drug during the early stage of administration of the agent, thus triggering earlier onset of an therapeutic effect by reducing the time seeded to reach systemic therapeutic levels. After a certain duration of time of administration, the drug can be released at a constant rate from the second layer which is an adhesive polymer which has a relatively high solubility of the drug, and so maintain a consistent long term therapeutic effect. The present device is particularly useful for transdermal delivery of highly potent, rapidly metabolized drugs having relatively narrow therapeutic indexes and which produce extremely undesirable side effects when overdosed, such as fentanyl and its derivatives, which are excellent therapeutic agents for treating acute postoperative or terminal cancer pains.

As illustrated in FIG. 1, the present invention provides a drug-containing laminated transdermal delivery system, comprising an impermeable backing or support layer (1), a first layer of a drug containing pressure sensitive adhesive (2a) having one surface laminated to the backing layer (1) and a second layer of a drug containing pressure-sensitive adhesive (2b) having one surface also laminated to the backing layer (1). The layers (2a and 2b) are made up of pressure-sensitive adhesive polymers having different solubilities for the drug. Prior to using, the opposing surfaces of layers (2a and 2b) are covered by a peelable backing layer (3). The surface area of each layer (2a and 2b) laminated to backing (1) is a function of the solubility of the drug in the adhesive and the release rate desired. Layers (2a and 2b) are adjacent each other on the support layer (1) and may, if desired, be adjoining Transdermal drug delivery devices comprising an impermeable backing layer having laminated thereto a pressure-sensitive adhesive layer containing a drug and covered by a peelable layer are well known in the art and are conventionally referred to as matrix devices. Methods of making such devices by casting an adhesive onto a backing layer and covering the same with a peelable layer are known. However, matrix devices having adjacent adhesive layers, each having a different solubility for the drug to be transdermally delivered are believed to be novel.

The impermeable support layer (1) is preferably 25–200 $\mu$m, more preferably 25–75 $\mu$m thick. The first laminated layer (2a) comprises an adhesive Polymer containing between about and 0.1~5.0 wt %, and preferably 05~20 wt % of the drugs and wherein the solubility of drug in the adhesive polymer is 1~20 mg/mL, preferably 2~10 mg/mL. The second laminated layer (2b) preferably comprises an adhesive polymer containing about 1~20% by wt of the drug and wherein the solubility of the drug in the adhesive polymer is preferably 30~200 mg/mL. Tile peelable hacking layer (3), being cast on top of the drug containing adhesive layers (2a and 2b), protects the laminated drug containing adhesive layers between manufacturing and storage and is readily stripped off prior to use.

The backing or support layer (1) of the transdermal delivery system of the present invention provides durability to the system. The support layer can be composed of either an occlusive (water impermeable) or a non-occlusive (water permeable) substance. However, it is preferred that the support layer be made of an occlusive substance in order to prevent or minimize diffusion of the drug from the laminated drug containing adhesive polymer layer into the support layer. The support layer is preferred to have a thickness of 25–200 $\mu$m for protection and support The desired durability of the support layer cannot be attained if the thickness is less than 25 $\mu$m while if it exceeds 200 $\mu$m, the resulting transdermal delivery system will be unable to have proper flexibility so that it can be properly adhered to curvaceous surfaces of the human body. The support layer can be made by using one or more members selected from the group consisting of polyester, polypropylene, polyethylene, polyvinyl chloride, polyurethane, and metal foil.

The essential feature of the present invention is that the first laminated layer (2a) and the second laminated layer (2b) comprise two adhesive polymers with different solubilities for the drug to be delivered. They are adjacently aligned or juxtaposed on the( support layer (1) such that each has a surface area for skin contact that will optimize the delivery of the drug for initial rapid delivery followed by a sustained delivery as previously mentioned.

Figure 2:
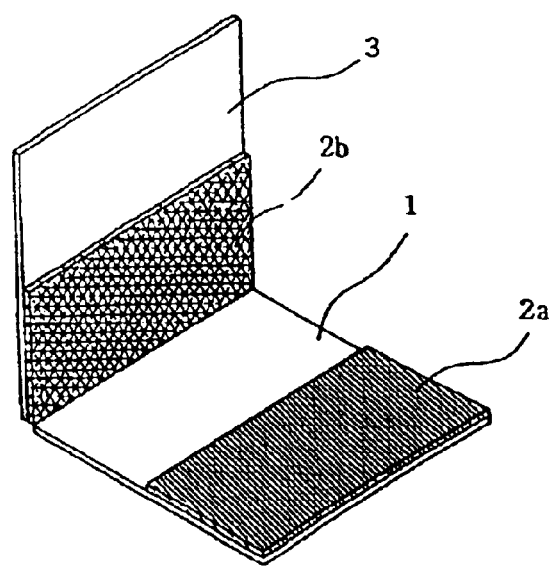
FIG. 2 shows a perspective view of the drug-containing laminated transdermal delivery system opened for illustrative purposes to show both drug containing layers with one layer (2a) adhering to support layer (1) and the second layer (2b) adhering to the peelable backing layer (3).

One embodiment of the present invention is a fentanyl-containing laminated transdermal delivery system. FIG. 2 illustrates such an embodiment in a manner to show that the first adhesive layer (2a) and the second adhesive layer (2b) are separate adhesives. As shown in FIG. 2, the first adhesive layer (2a) is attached to the support layer (1) while the second adhesive layer (2b) is affixed to the peelable hacking layer (3). FIG. 1 shows the same embodiment with the support layer (1) forming one side of device 10 and the peelable layer (3) forming the opposing side of this device. The adhesive layers (2a and 2b) are sandwiched between the outer layers in a side bad side relationship. Obviously, the adhesive layers (2a and 2b) are laminated to and adhere more tightly to the support layer (1) than to the peelable layer (3). Otherwise, the peelable layer (3) could not be removed at tie time of application to expose the surface of layers (2a and 2b) for attachment to the skin.

The first adhesive layer (2a) comprises pressure-sensitive adhesive polymer having a solubility for fentanyl within a range of 1.0~20 mg/mL, preferably 2–10 mg/mL Since fentanyl can be rapidly released within a short period of time from the first adhesive layer there will be almost no fentanyl remaining in the layer about one day after the onset of fentanyl release. Therefore, the rapid delivery of fentanyl via the systemic circulation during the early stages of administration facilitated. This initial burst of fentanyl is followed by delivery of fentanyl at a more sustained rate from the second adhesive 1 layer thereby enabling the present system to reduce the lag time between onset of administration and the obtaining of effective serum levels of fentanyl for rapid onset and sustained pain control. If the solubility of fentanyl in the first adhesive layer is less than 1.0 mg/mL, the desired rapid release of fentanyl during the early stage of administration cannot be attained because the amount of fentanyl dissolved in the adhesive polymer is too little. However, the fentanyl cannot be rapidly released if the solubility exceeds 20 mg/mL, which will undesirably increase the amount of fentanyl remaining in the layer after use.

The flux of fentanyl from the first laminated layer through the skin was tested using the method described in *J. Pharm. Sci.*, (1983), 72: 968, hereby incorporated by reference, and it was shown to be 0.2~3.0 $\mu$g/cm$^2$/hr. The amount of fentanyl contained in the first adhesive layer is preferably 0.01~0.5 mg/cm$^2$, and most preferably 0.05~02 mg/cm$^2$. From a quantitative point of view, the amount or concentration of fentanyl in the first adhesive layer is preferably 0.1~5.0 wt % and most preferably 0.5~2.0 wt %. If the amount of fentanyl is less than 0.1 wt %, the desired release rate of fentanyl cannot be attained. However, if the amount of fentanyl exceeds 5.0 wt %, fentanyl cannot be completely dissolved or extracted as a crystallized form because it exceeds the limit of solubility of fentanyl.

The first layer may also serve to mediate the adhesion to the skin for transdermal delivery of fentanyl. Therefore, the polymer used to make the first laminated layer preferably has an adhesive property and the preferred adhesive polymers are silicone adhesives or modified silicone adhesives such as the polydimethylsiloxane.

The second adhesive layer (2b) of the present invention is the second drug containing layer comprising fentanyl and pressure-sensitive adhesive polymers having a solubility of fentanyl within a range of 30~200 mg/ml preferably 50~150 mg/mL. Therefore, the second drug containing adhesive layer can mediate the slow release of fentanyl for a relatively long period of time and also maintain a constant fentanyl concentration in blood. If the solubility of fentanyl in the adhesive polymer of the second layer is less than 30 mg/mL the release rate of fentanyl becomes too rapid to maintain the desired constant blood concentration. However, if the solubility of fentanyl in the adhesive polymer of the second layer exceeds 200 mg/mL, the rate of fentanyl release becomes so slow that remaining fentanyl in the device after use increases to an undesired amount.

The flux of fentanyl from the second adhesive layer through the skin is preferably within the range of 0.5~6.0 $\mu$g/cm$^2$/hr, and more preferably within the range of 1.0~4.0 $\mu$g/cm$^2$/hr, as tested using the method described in *J. Pharm. Sci.*, (1983), 72: 968. The amount of fentanyl contained in the second adhesive layer is preferably within the range of 0.1~2.0 mg/cm$^2$, and more preferably within the range of 0.2~0.6 mg/cm². From a quantitative point of view, the amount of fentanyl is preferably 1.0~20 wt % of that of the second adhesive layer (2b), and more preferably 2.0~6.0 wt %. If the amount of fentanyl is less than 1.0 wt %, the desired long-term release of fentanyl cannot be achieved because the amount of fentanyl contained in the adhesive layer is not sufficient. However, if the amount of fentanyl exceeds 20 wt %, the fentanyl cannot be completely dissolved and precipitates as a crystallized form.

The second adhesive layer (2b) may also serve to mediate the adhesion of the laminated layer for transdermal delivery of fentanyl. Therefore, the polymer used to prepare the second laminated layer preferably has an adhesive property and the preferred adhesive polymer is one or more members selected from the is group consisting of acrylate adhesives, acrylate copolymer adhesives, anti isobutylene adhesives. The more preferred adhesive polymers for the second laminated layer are polyacrylate adhesives.

As described above, the drug containing adhesive layers (2a and 2b) of the present invention can rapidly establish a blood concentration of the fentanyl at an effective level during the early stage of administration and still maintain a sustained delivery of the drug. This is achieved by rapid release from the first adhesive layer which has a lower solubility of the drug, followed up by constant drug delivery from the second adhesive layer (2b), which has a higher solubility of the drug. Even after the first adhesive layer is depleted of the drug, the second adhesive layer can continue to supply sufficient amounts of the drug at a constant rate. Because of rapid release from the first adhesive layer, the time required to reach an effective blood concentration can be reduced to obtain the desired drug effect. Therefore, the device of the present invention is particularly useful for fentanyl delivery because it provides for both a rapid onset and a relatively long duration of an analgesic effect and thus can be used in relieving acute pains accompanied following surgery or at the terminal stage of a cancer.

The basal surface area for skin contact for the adhesive layers (2a and 2b) are generally within the range of 5~50 cm², and preferably within the range of 10~40 cm². It is also preferred that the surface ratio between the first adhesive layer and the second adhesive layer is within the range of 1:9 to 3:2, and more preferably within the range of 1:4 to 2:3. Therefore, within these parameters, the effective amount of fentanyl transdermally delivered should be sufficient to shorten the time needed to reach an effective blood concentration of fentanyl as well as prevent any side effects due to excessive administration of fentanyl, and still provide for a relatively long-term analgesic effect Optionally, i skin penetration enhancer may be added in the first and/or second adhesive layers (2a, 2b) in order to elevate the rate of drug flux across the skin. Such a penetration enhancer is preferably one or more members selected from the group consisting of ethanol, myristic acid, methyl myristate, polyethylene glycol monolaurate, propylene glycol and its derivatives, fatty acids having 8~20 carbon atoms, glycolic acid, N-methylpyrrolidone, dimethyl sulfoxide, linoleic acid, and pyirrolidone and its deriavatives.

The peelable backing layer (3) acts as a release liner that is stripped off from the transdermal delivery system prior to use so that drug-containing laminated layers (2a and 2b) can be exposed. This layer is made from polymers well known in the art which are either peelable by nature or from polymers which are rendered impermeable to the drug by treating the surface with silicone or fluorocarbon compounds which are readily stripped off.

Figure 3:
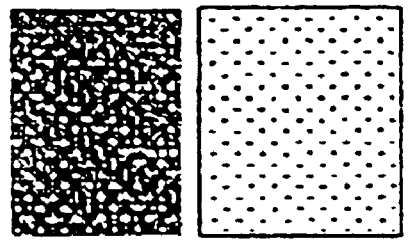
FIGS. 3 (a)-(d) fire sectional views showing different configurations of adhesive layers (2a and 2b) that can be laminated to a support layer (not shown) and covered by a peelable layer (not shown).
Figure 3:
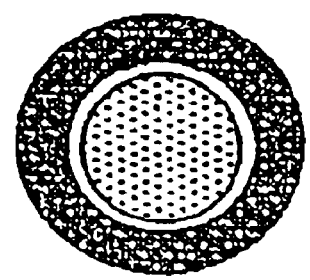
Figure 3:
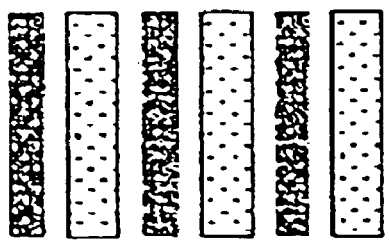
Figure 3:
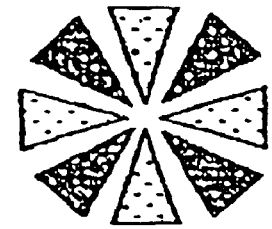

The steady-state flux of the drug, i.e. fentanyl, through the skin via the dual adhesive transdermal delivery system according to the present invention is preferably within the range of 0.5~8.0 µg/cm²/hr, and more preferably within the range of 1.0~6.0 µg/cm²/hr, and is usable for up to 3 days. The flux of fentanyl for the first day is preferably within the range of 2.0~8.0 µg/cm²/hr, and more preferably within the range of 3.0~5.0 µg/cm²/hr. The flux of fentanyl after the first day is preferably within the range of 0.5~6.0 µg/cm²/hr, and more preferably within the range of 1.0~4.0 µg/cm²/hr. FIGS. 3(a)–(d) illustrate other representative configurations for the first and second adhesive layers (2a and 2b) that may be used for the present invention As shown in FIG. 3(a), the shape of the layers (2a and 2b) can be a rectangular. As shown in FIG. 3(b) layers (2a and 2b) can be concentric circles. FIG. 3(c) shows layers (2a and 2b) as alternating rectangles and FIG. 3(d) shows layers (2a and 2b) in a generally circular arrangement is alternating triangles. These art illustrative only and other arrangements in a patterned or random order, limited only by functionality, may be utilized.

This invention is further illustrated by the following examples. These examples should not be construed as limiting the scope of this invention in any manner.

EXAMPLE 1

A first adhesive layer (2a, 40 µm thick) containing 0.7 wt % of fentanyl base was prepared as follows. An adhesive solution was prepared by dissolving fentanyl base in a 60 wt % solution of polydimethylsiloxane dissolved in ethyl acetate (Dow Coming BIO-PSA 7-4302) followed by 20 min drying at 70° C. The adhesive solution was then cast to cover half the surface of a support layer (1) comprised of an aluminum-coated polyester film (3M Scotchpak 1009).

A second adhesive layer (2b, 40 µm thick) containing 10 wt % of fentanyl base was prepared as follows. Another adhesive solution was prepared by dissolving fentanyl base in a 385 wt % solution of an acrylate/vinylacetate copolymer dissolved in ethyl acetate (National starch DUROTAK 97-4098) followed by 20 min driving at 70° C. The adhesive solution was then cast to cover half the surface of i peelable backing layer (3) of fluorocarbon-coated polyester film (3M, 1022).

As shown in FIG. 2, the first and the second adhesive layers laminated to their respective film supports were arranged so as to form a laminated sandwich sheet which fit the first adhesive layer (2a) into the uncast region of the peelable backing layer (3), and to fit the second adhesive layer (2b) into the uncast region of the support layer (1). The resulting laminated sheet was cut in order to generate a surface containing 3 cm² of the first adhesive layer (2a) and 7 cm² of the second adhesive layer (2b) in order to obtain the final laminated fentanyl device 10 containing a dual adhesive system for transdermal delivery of fentanyl. For conventional application the peelable layer (3) would be stripped from the device exposing one surface of each adhesive layer (2a, 2b) which would be affixed to the skin and held in place by the adhesive properties of each layer.

For in vitro testing the above described transdermal fentanyl delivery system was then evaluated for skin flux after the peelable layer was stripped from the device. Particularly, the diffusion cell for testing was prepared which of the volume was 50 ml and sample area was 10 cm². The evaluation for skin flux proceeded by a conventional method as described in *J. Pharm. Sci.*, (1983), 72: 968, hereby incorporated by reference. The flux of fentanyl through cadaver skin was measured using the above laminated transdermal fentanyl delivery system after cutting it into a shape which fit into a diffusion cell The result was 4.0 $\mu g/cm^2/$ hr for the first 24 hrs after administration, and 1.5 $\mu g/cm^2/hr$ for the period of between 24–72 hrs after administration.

As a way to indirectly measure the effect of the transdermal delivery system of the present invention on the analgesic effect and the onset of its expression, the time for the cumulative amount of fentanyl released from the system to reach 50 $\mu g/cm^2$ was measured and it was 12 hrs. The amount of fentanyl remaining in the system after 72 hrs of administration was 32% of the total amount of fentanyl present in the initial laminated system, indicating 68% of fentanyl was delivered is during that period.

EXAMPLE 2

A laminated fentanyl containing adhesive system was obtained using the same method described in Example 1 with the exception that the concentration of fentanyl base in the second adhesive layer (2b) was 13 wt % and the surface area of the first adhesive layer (2a) and the second adhesive layer (2b) was each 5 cm².

The flux of fentanyl of the system was measured as 4.6 $\mu g/cm^2/hr$ for the first 24 hrs after administration, and 1.4 $\mu g/cm^2/hr$ for the period of between 24–72 hrs after administration. The time for the cumulative amount of fentanyl released from the system of the present invention to reach 50 $\mu g/cm^2$ was 10 hrs, and the amount of fentanyl remaining in the system after 72 hrs of administration was 29%.

EXAMPLE 3

A laminated fentanyl containing adhesive system was obtained using the same method as in the Example 1 with the exception of the first adhesive layer (2a) having a 60 $\mu m$ thick adhesive layer with 1.0 wt % concentration of fentanyl base, the second adhesive layer (2b) having a 60 $\mu m$ thick adhesive layer with 13 wt % of fentanyl base, and the surface areas of the first adhesive layer (2a) and the second adhesive layer (2b) being 7 cm² and 3 cm², respectively.

The flux of fentanyl of the system was measured as 5.2 $\mu g/cm^2/hr$ for the first 24 hrs after administration, and 1.2 $\mu g/cm^2/hr$ for the period of between 24–72 hrs after administration. The time for the cumulative amount of fentanyl released from the system of the present invention to reach 50 $\mu g/cm^2$ was 7 hrs and the amount of fentanyl remaining in the system after 72 hrs of administration was 28%

EXAMPLE 4

A laminated fentanyl containing adhesive system was obtained using the same method as in the Example 1 with the exception of the following. A 32.5 wt % solution of an acrylate polymer(Monsanto, Gelva 737) dissolved in a mixed solvent of ethyl acetate, toluene and ethanol was used to form the second adhesive layer. The first adhesive layer (2a) having a 60 $\mu m$ thick adhesive layer with 0.7 wt % of fentanyl base, the second adhesive layer (2b) having a 60 $\mu m$ thick adhesive layer with 6 wt % concentration of fentanyl base. The surface areas of the first adhesive layer (2a) and the second adhesive layer (2b) were 2 cm²and 8 cm², respectively.

The flux of fentanyl was measured as 4.0/cm²/hr for the first 24 hrs after administration, and 1.4 $\mu g/cm^2/hr$ for the period of between 24~72 hrs after administration. The time for the cumulative amount of fentanyl released from the system of the present invention to reach 50 $\mu g/cm^2$ was 12 hrs, and the amount of fentanyl remaining in the system after 72 hrs of administration was 29%.

EXAMPLE 5

In A laminated fentanyl containing adhesive system was obtained using the same method as in Example 1 with the exception of the following. An additional 10 $\mu m$ thick adhesive layer of 60 wt % solution of polydimethylsiloxane (Dow Corning BIO-PSA 7-4302) dissolved in ethyl acetate without fentanyl, was cast on top of the peelable backing layer (3). In addition, the fentanyl containing second adhesive layer (2b, the acrylate/vinylacetate copolymer of Example 1) containing 12 wt % fentanyl base and having a thickness of 30 $\mu m$ was cast on the polydimethylsiloxane making an adhesive layer having a total thickness of 40 $\mu m$. The first adhesive layer, having a thickness of 40 $\mu m$ was the same as in Example 1. In other words, the total skin contact surface of the first and second adhesive layers was a polydimethylsiloxane polymer.

The flux of fentanyl was measured as 4.1 $\mu g/cm^2/hr$ for the first 24 hrs after administration, and 1.6 $\mu g/cm^2/hr$ for the period between 24–72 hrs after administration. The time for the cumulative amount of fentanyl released from the system of this Example to reach 50 $\mu g/cm^2$ was 12 hrs and the amount of fentanyl remaining in the system after 72 hrs of administration was 3%. The flux and the remaining amount of fentanyl were very close to those in the Example 1. However, the adhesiveness of the additionally added siloxane adhesive layer was shown to be superior to that of the second adhesive layer (2b) in the Example 1, during the period of 72 hrs.

COMPARATIVE EXAMPLE 1

Tests on the flux and the remaining amount of fentanyl were carried out by using the conventional reservoir fentanyl patch, Durogesic®. The conventional reservoir fentanyl patch used was a rectangular patch with round edges. The patch contains a fentanyl base (2.5 mg)-containing gel, adequate amounts of lydroxyethyl cellulose, ethanol and purified water, which were filled into the space between a support layer consisting of polyester/ethylenevinyl acetate laminate film and a release controlling layer consisting of ethylenevinyl acetate. The release controlling layer was laminated with an adhesive layer and a peelable backing layer.

The flux of fentanyl was measured at 2.8 $\mu g/cm^2/hr$ for the first 24 hrs after administration, and 1.3 $\mu g/cm^2/hr$ for the period of between 24–72 hrs after administration. The time for the cumulative amount of fentanyl released from the system of the present invention to reach 50 $\mu g/cm^2$ was 16 hrs and the amount of fentanyl remaining in the (composite after 72 hrs of administration was 46%. When this Example is compared with the results obtained using the dual adhesive laminated system of Example 5 it is seen that the initial flux of fentanyl, the sustained release from 24 to 72 hours, the time taken to reach a target of 50 $\mu g/cm^2$ and the residual fentanyl left in the device from Example 5 is superior in each area tested to that of the commercial system.

COMPARATIVE EXAMPLE 2

A pressure-sensitive adhesive having a 50 $\mu m$ thick adhesive layer as well as 12 wt % of fentanyl base was prepared by casting an adhesive solution on top of a support layer made of aluminum-coated polyester film (3M, Scotchpak 1009). The adhesive solution was prepared by dissolving fentanyl base in a 38.5 wt % solution (National starch DUROTAK 97-4098) in which an acrylate/vinylacetate copolymer as an adhesive is dissolved in ethyl acetate, followed by 20 min drying at 70° C. A peelable backing layer made of a fluorocarbon-coated polyester film (3M, Scotchpak 1022) was cast on top of the sheet obtained and was cut to generate a 10 cm² composite of three laminated layers.

The flux of fentanyl was measured as 3.0 $\mu g/cm^2/hr$ for the first 24 hrs after administration, and 1.5 $\mu g/cm^2/hr$ for the period of between 24–72 hrs after administration. The time for the cumulative amount of fentanyl released from the system of the present invention to reach 50 $\mu g/cm^2$ was 15 hrs and the amount of fentanyl remaining in the composite after 72 hrs of administration was 40%. As in the case with Comparative Example 1, when the data from this Example is compared with the results in Example 5 it is seen that the initial flux of fentanyl, the sustained release from 24 to 72 hours, the time taken to reach a target of 50 $\mu g/cm^2$ and the residual fentanyl left in the device from Example 5 is superior in each area tested to that obtained in this Example.

Although the above examples and descriptions demonstrate the formation of a fentanyl-containing laminate adhesive system for the transdermal delivery of fentanyl, the same techniques can be utilized to deliver other active permeants or drugs through skin or mucosa Therefore, the above examples are but illustrative of a complete and preferred embodiment which may be employed in operation of the present invention. The invention is directed to the discovery of a drug-containing dual adhesive laminated transdermal delivery system wherein the drug can be rapidly released during the early stages of administration by means of one adhesive layer having limited solubility for the drug and reach a therapeutic level systemically and maintains a persistent long-term therapeutic effect by means of a second adhesive layer having a greater solubility for the drug. Therefore, within the guidelines presented herein, a certain amount of experimentation to obtain optimal formulations can be readily carried out by those skilled in the art. Therefore, the invention is limited in scope only by the following claims and functional equivalents thereof.

What is claimed is:

1. A dual drug containing adhesive transdermal drug delivery system comprising:
   1) a support layer,
   2) pressure-sensitive adhesive layers comprising a first drug containing adhesive layer and a second drug containing adhesive layer, each of said layers having a proximal surface and a distal surface,
   wherein said first and second adhesive layers are positioned adjacent to each other, the distal surface of each said adhesive layer is laminated to said support layer, the solubility of a drug in said first adhesive layer is within the range of 1.0 to 20 mg/ml, and the solubility of the drug in said second adhesive layer is within the range of 30 to 200 mg/ml, and
   3) a peelable backing layer positioned over and laminated to the proximal surface of said first and second adhesive layers.

2. The dual drug containing adhesive transdermal drug delivery system of claim 1, wherein the drug content of in said first adhesive layer is within the range of 0.1 to 5.0 wt %.

3. The dual drug containing adhesive transdermal drug delivery system of claim 1, wherein the drug content of in said second adhesive layer is within the range of 1.0 to 20 wt %.

4. The dual drug containing adhesive transdermal drug delivery system of claim 1, wherein the adhesive polymer of said first adhesive layer is a member selected from the group consisting of silicone adhesives, modified silicone adhesives, and mixtures thereof.

5. The dual drug containing adhesive transdermal drug delivery system of claim 1, wherein the adhesive polymer of said second adhesive layer is a member selected from the group consisting of acrylate adhesives, acrylate copolymer adhesives, isobutylene adhesives, and mixtures thereof.

6. The dual drug containing adhesive transdermal drug delivery system of claim 1, wherein the first or second adhesive layer further comprises a penetration enhancer.

7. The dual drug containing adhesive transdermal drug delivery system of claim 1, wherein the drug is a member selected from the group consisting of antibiotics; antiviral agents; analgesic agents; anorexics; anthelmintics; antiarthritics; antiasthmatic agents; anticonvulsants; antidepressants; antidiabetic agents; antidiarrheals; antihistamines; antiinflammatory agents; antimigraine agents; antinauseants; antineoplastics; antiparkinsonism drugs; antipruritics; antipsychotics; antipyretics; antispasmodics; anticholinergics; sympathomimetics; xanthine derivatives; cardiovascular drugs; antiarrhythmics; antihypertensives; diuretics; antidiuretics; vasodilators; vasoconstrictors; decongestants; hormones; immunosuppressives; muscle relaxants; parasympatholytics; psychostimulants; sedatives; and tranquilizers.

8. The dual drug containing adhesive transdermal drug delivery system of claim 1, wherein the drug is an analgesic agent.

9. The dual drug containing adhesive transdermal drug delivery system of claim 1, wherein the drug is fentanyl.

10. The dual drug containing adhesive transdermal drug delivery system of claim 9, wherein the content of fentanyl in said first adhesive layer is within the range of 0.1 to 5.0 wt % the content of fentanyl in said second adhesive layer is within the range of 1.0 to 20 wt %.

11. The dual drug containing adhesive transdermal drug delivery system of claim 9, wherein the adhesive polymer of said second adhesive layer is an acrylate copolymer adhesive.

12. The dual drug containing adhesive transdermal drug delivery system of claim 9, wherein the first and the second adhesive layers of said dual have a surface ratio within the range of 1:9 to 3:2.

13. The dual drug containing adhesive drug delivery system of claim 9, wherein the first and the second adhesive layers have a surface ratio within the range of 1:4 to 2:3.

* * * * *